(12) United States Patent
Dawes et al.

(10) Patent No.: US 7,671,227 B2
(45) Date of Patent: Mar. 2, 2010

(54) ASYMMETRIC BIS-SILANES AND METHODS FOR MAKING AND THEIR USE

(75) Inventors: Steven B. Dawes, Corning, NY (US); James R. Matthews, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/998,227

(22) Filed: Nov. 29, 2007

(65) Prior Publication Data

US 2008/0207937 A1 Aug. 28, 2008

Related U.S. Application Data (60) Provisional application No. 60/904,126, filed on Feb. 28, 2007.

(51) Int. Cl.
*C07F 7/04* (2006.01)
(52) U.S. Cl. .......................... 556/465; 430/56
(58) Field of Classification Search ............... 428/450; 546/14; 556/400, 405
See application file for complete search history.

(56) References Cited

U.S. PATENT DOCUMENTS 2,624,721 A * 1/1953 Hatcher et al. ............. 528/34
6,870,181 B2 * 3/2005 Zhang et al. ............... 257/40

2007/0195576 A1 * 8/2007 Imada et al. ............... 365/103

FOREIGN PATENT DOCUMENTS

WO 2004/006300 1/2004

OTHER PUBLICATIONS

Sigalov et al., Derivatives of methyl substituted trans-1,2 disilylethylene, Izvestiya Akademii Nauk SSSR, Seriya Khimicheskaya (1974), (9), 2066-2070.*
Baryshok et al.,[(Ethoxycarbonyl)alkyl]trifluorosilanes, Metalloorganicheskaya Khimiya (1992), 5(6), 1306-1312.*
L.N. Lewis, "On the Mechanism of Metal Colloid Catalyzed Hydrosilylation: Proposed Explanations for Electronic Effects and Oxygen Cocatalysis", J. Am Chem. Soc., 1990, vol. 112, No. 16, pp. 5998-6004.
B. O'Regan et al., "A low-cost, high-efficiency solar cell based on dye-sensitized colloidal $TiO_2$ Films", Nature, vol. 353, Oct. 24, 1991, pp. 737-740.
D. Zhang et al., "Room-Temperature Synthesis of Porous Nanoparticulate $TiO_2$ Films for Flexible Dye-Sensitized Solar Cells", Advanced Functional Materials, 2006, vol. 16, pp. 1228-1234.
M.G. Voronkov, et al., "Methyl-substituted trans 1,2-Disilylethylene Derivatives", Bulletin of the Academy of Sciences of the USSR, Division of Chemical Sciences, vol. 23, 1974, pp. 1984-1988.

* cited by examiner

*Primary Examiner*—Sikarl A Witherspoon
*Assistant Examiner*—Chukwuma O Nwaonicha
(74) *Attorney, Agent, or Firm*—John L. Haack (57) ABSTRACT

An asymmetric bis-silane compound of the formula $$A_3Si-R^1-SiB_3$$

where A, B, and $R^1$ are as defined herein, and to methods for making the bis-silane compound and their use to form layers or films of metal oxide particles, and which layers or films adhere to a suitable substrate. The materials and methods can be used, for example, to make photoactive devices.

12 Claims, 6 Drawing Sheets

ASYMMETRIC BIS-SILANES AND METHODS FOR MAKING AND THEIR USE

CLAIMING BENEFIT OF PRIOR FILED U.S. APPLICATION

This application claims the benefit of U.S. Provisional Application Ser. No. 60/904,126, filed on Feb. 28, 2007. The content of this document and the entire disclosure of publications, patents, and patent documents mentioned herein are incorporated by reference.

BACKGROUND

The disclosure relates generally to compounds, compositions, and methods for forming cohesive layers or films of particles and where the cohesive layers or films adhere to a suitable substrate.

SUMMARY

In general terms, the claimed invention relates to certain asymmetric bis-silane compounds having differential reactivity and to methods for making the bis-silane and their use to form cohesive layers or films of metal oxide particles, which layers or films can optionally adhere to a suitable substrate. The materials and methods can be used, for example, to make photoactive devices.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In embodiments the disclosure provides compounds, compositions, and methods for forming high surface area particle layers and devices having the layers in which the particles adhere to each other and to a substrate upon which the particle layers are assembled.

In embodiments the disclosure provides a compound of the general formula $$A_3Si-R^1-SiB_3$$

where $R^1$ is a divalent spacer group selected from certain hydrocarbyl groups, such as aliphatic and aromatic moieties;

A is a monovalent group which can react a nucleophile;

B is a monovalent group which can also react with a nucleophile, but at a different rate compared to the A groups. The relative rate of reaction of A and B with respect to nucleophiles is sufficiently different to permit selective or stepwise reaction of the A groups over the B groups (i.e., reactivity of A>B) or the converse (i.e., reactivity of A<B). "Nucleophiles" and like terms refer to electron donors or Lewis bases, such as carbon, oxygen, nitrogen, sulfur, and like nucleophiles, and include metal oxide surface bound or surface associated groups, for example, hydroxyl (—OH), thiol (—SH), amine (—NH—), or their corresponding ionic forms, and like surface groups. "Metal oxide surface" and like terms refer to any part of the metal oxide particle which is accessible by, for example, another reagent or molecule, such as a bis-silane, a conjugate such as a first reaction product of a bis-silane and a metal oxide particle, a dye, water, oxygen, or like molecules or entities. For additional definitions, descriptions, and methods of silica materials and related metal oxide materials, see for example, R. K. Iler, *The Chemistry of Silica*, Wiley-Interscience, 1979.

In embodiments the disclosure provides a compound of the formula (I)

$$(R^2O)_3Si-R^1-SiX_3 \qquad (I)$$

where $R^1$ is a divalent hydrocarbyl spacer group selected from saturated or unsaturated —($C_1$-$C_{20}$)alkylene-, ($C_1$-$C_4$)alkyl substituted saturated or unsaturated —($C_1$-$C_{20}$)alkylene-, —Ar—, ($C_1$-$C_4$)alkyl substituted —Ar—, —($CH_2$)$_k$—Ar—($CH_2$)$_k$—, ($C_1$-$C_4$)alkyl substituted —($CH_2$)$_k$—Ar—($CH_2$)$_k$—, —Ar—Ar—, ($C_1$-$C_4$)alkyl substituted —Ar—Ar—, —($CH_2$)$_k$—Ar—Ar—($CH_2$)$_k$—, ($C_1$-$C_4$)alkyl substituted —($CH_2$)$_k$—Ar—Ar—($CH_2$)$_k$—, —($CH_2$)$_k$—Ar—($CH_2$)$_k$—Ar—($CH_2$)$_k$—, ($C_1$-$C_4$)alkyl substituted —($CH_2$)$_k$—Ar—($CH_2$)$_k$—Ar—($CH_2$)$_k$—, —Ar—O—Ar—, ($C_1$-$C_4$)alkyl substituted —Ar—O—Ar—, —($CH_2$)$_k$—Ar—O—Ar—($CH_2$)$_k$—, ($C_1$-$C_4$)alkyl substituted —($CH_2$)$_k$—Ar—O—Ar—($CH_2$)$_k$—, Het, ($C_1$-$C_4$)alkyl substituted —Het—, —($CH_2$)$_k$—Het—, ($C_1$-$C_4$)alkyl substituted —($CH_2$)$_k$—Het—, —($CH_2$)$_k$—Het—($CH_2$)$_k$—, ($C_1$-$C_4$)alkyl substituted —($CH_2$)$_k$—Het—($CH_2$)$_k$—, —Ar—($CH_2$)$_k$—, ($C_1$-$C_4$)alkyl substituted —Ar—($CH_2$)$_k$—, Ar'—CH=, or ($C_1$-$C_4$)alkyl substituted Ar'—CH=;

$R^2$ is a monovalent group each independently a branched or unbranched, saturated or unsaturated —($C_1$-$C_6$)alkyl, —Ar or ($C_1$-$C_4$)alkyl substituted —Ar;

X is halo, and wherein compound of the formula (I) is other than ($CH_3CH_2$—O)$_3$Si—$CH_2$—$CH_2$—SiCl$_3$.

In embodiments $R^1$ can be a non-hydrocarbyl divalent spacer group such as an amine of the formula —NR$^3$— or a diamine of the formula —NR$^3$—R$^1$—NR$^3$— where R$^1$ is a defined above, and R$^3$ can be H, or saturated or unsaturated —($C_1$-$C_4$)alkyl.

In embodiments $R^1$ can be a divalent spacer group such as a dye compound which has been modified to include the aforementioned asymmetric bis-silane functionality.

In embodiments the disclosure provides the above compounds of the formula (I), including ($CH_3CH_2$—O)$_3$Si—$CH_2$—$CH_2$—SiCl$_3$, for use in compositions and methods for preparing layers or films of metal containing particles which adhere to a suitable substrate. The materials and methods can be used to make devices, for example, photoactive or photosensitive devices.

In embodiments, halo or halide includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

"Alkyl" includes linear alkyls, branched alkyls, and cycloalkyls.

"Substituted alkyl" or "optionally substituted alkyl" refers to an alkyl substituent, which includes linear alkyls, branched alkyls, and cycloalkyls, having from 1 to 4 optional substituents selected from hydroxyl (—OH), halogen, amino (—NH$_2$), nitro (—NO$_2$), alkyl, acyl (—C(=O)R), alkylsulfonyl (—S(=O)$_2$R) or alkoxy (—OR). For example, an alkoxy substituted alkyl, can be a 2-methoxy substituted ethyl of the formula —CH$_2$—CH$_2$—O—CH$_3$, a 1-dialkylamino substituted ethyl of the formula —CH$_2$(NR$_2$)—CH$_3$, and like substituted alkyl substituents.

"Aryl" includes a mono- or divalent-phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents. In embodiments Ar or Aryl can include an aromatic dye compound which can be modified to include the asymmetric bis-silane functional groups.

"Het" includes a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl, or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. In embodiments Het includes a heteroaromatic or heterocyclic dye compound which can be modified to include the asymmetric bis-silane functional groups. One suitable dye is, for example, cis-(NCS)$_2$bis(4,4'-dicarboxy-2,2'bipyridine)-ruthenium(II) (See Sommeling et al., 2000).

The carbon atom content of various hydrocarbon-containing moieties is indicated by a prefix designating a lower and upper number of carbon atoms in the moiety, i.e., the prefix C$_{i-j}$ indicates a moiety of the integer "i" to the integer "j" carbon atoms, inclusive. Thus, for example, (C$_1$-C$_7$)alkyl or C$_{1-7}$alkyl refers to alkyl of one to seven carbon atoms, inclusive, and (C$_1$-C$_4$)alkyl or C$_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to for example aging of a formulation with a particular initial concentration or mixture, and amounts that differ due to mixing or processing a formulation with a particular initial concentration or mixture. Whether modified by the term "about" the claims appended hereto include equivalents to these quantities.

"Consisting essentially of" in embodiments refers, for example, to a single compound, mixture of compounds, or a composition, the method of using a compound or composition to make metal oxide particle films or layers, and articles or devices of the disclosure, and can include the components or steps listed in the claim, plus other components or steps that do not materially affect the basic and novel properties of the compounds, composition, articles, and methods of use of the disclosure, such as the particular substrates, the particular bireactive or bis-silane, the particular metal oxide or mixed metal oxide, or like structure, material, or process variables selected. Items that may materially affect the basic properties of the components or steps of disclosure or may impart undesirable characteristics to the present disclosure include, for example, decreased or loss of differential reactivity of the bis-silane, decreased surface area of the silane modified metal oxide films or layers, decreased adhesion of the silane modified metal oxide films or layers to a suitable substrate, and like characteristics. In embodiments, the compounds, the composition, the articles or devices, or the methods of the present disclosure preferably eliminate or avoid such undesirable characteristics. Thus, the claimed invention may suitably comprise, consist of, or consist essentially of: a compound of the formula (I) as defined herein; a composition of the reaction product including a compound of formula (I) and a metal oxide particle, as defined herein; a photovoltaic device including the aforementioned composition, a substrate, and an optional photosensitizer material or like material; or a method of making the photovoltaic device as defined herein.

The indefinite article "a" or "an" and its corresponding definite article "the" as used herein means at least one, or one or more, unless specified otherwise.

Specific and preferred values listed below for radicals, substituents, and ranges, are for illustration only; they do not exclude other defined values or other values within defined ranges for the radicals and substituents. The compounds of the disclosure include compounds of formula (I) and like compounds having any combination of the values, specific values, more specific values, and preferred values described herein.

Specifically, C$_{1-4}$alkyl can be methyl, ethyl, propyl, isopropyl, butyl, iso-butyl, sec-butyl, tert-butyl; C$_{1-7}$alkyl can be methyl, ethyl, propyl, isopropyl, butyl, iso-butyl, sec-butyl, tert-butyl, pentyl, 3-pentyl, hexyl, or heptyl; (C$_{3-12}$)cycloalkyl can be cyclopropyl, cyclobutyl, cyclopentyl, cyclohexyl, cycloheptyl, cyclooctyl, bicyclic, or multi-cyclic substituents, such as of the formulas $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; —C(=O)alkyl or ($C_{2-7}$)alkanoyl can be acetyl, propanoyl, butanoyl, pentanoyl, 4-methylpentanoyl, hexanoyl, or heptanoyl; aryl (Ar) can be phenyl, naphthyl, anthracenyl, phenanthrenyl, fluorenyl, tetrahydronaphthyl, or indanyl; Het can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, —$(CH_2)_k$— can be a —($C_{1-20}$alkylene)- when k is an integer from 1 to about 20, which can be methylenyl, ethylenyl, propylenyl, butylenyl, pentylenyl, 3-pentylenyl, hexylenyl, heptylenyl, octylenyl, nonylenyl, decylenyl, and like homologs.

Specifically, —$(CH_2)_k$— can be a —($C_{1-7}$alkylene)- when k is an integer from 1 to about 7, or from 1 to about 5, which can be methylenyl, ethylenyl, propylenyl, butylenyl, pentylenyl, 3-pentylenyl, hexylenyl, or heptylenyl.

Specifically, —$(CH_2)_k$— can be a —($C_{1-4}$alkylene)- when k is an integer from 1 to about 4, which can be methylenyl, ethylenyl, propylenyl, or butylenyl.

A specific value for Het includes a five- (5), six- (6), or seven- (7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic Het diradical thereto.

A specific compound is of the formula (I) wherein $R^1$ can be, for example, —Ar—, or ($C_1$-$C_4$)alkyl substituted —Ar—, where Ar can be, for example, an ortho-, meta-, or para-substituted —$C_6H_4$—;

Another specific compound is of the formula (I) wherein $R^1$ can be, for example, —$CH_2$—Ar—$CH_2$—, or ($C_1$-$C_4$) alkyl substituted —$CH_2$—Ar—$CH_2$—, where Ar can be, for example, an ortho-, meta-, or para-substituted —$C_6H_4$—;

Another specific compound is of the formula (I) wherein $R^1$ can be, for example, —Ar—$CH_2$—, or ($C_1$-$C_4$)alkyl substituted —Ar—$CH_2$—, where Ar can be, for example, an ortho-, meta-, or para-substituted —$C_6H_4$—; such as —$C_6H_4$—$CH_2$—, or ($C_1$-$C_4$)alkyl substituted —Ar—$CH_2$—, such as —$C_6H_3$(R)—$CH_2$—, or optionally alkyl substituted —$C_6H_4$—CH(R)—, where R can be ($C_1$-$C_4$)alkyl or a substituted ($C_1$-$C_4$)alkyl.

Another specific compound is of the formula (I) wherein $R^1$ can be, for example, Ar'—CH=, or ($C_1$-$C_4$)alkyl substituted Ar'—CH=, where each Ar' is an aryl substituent connected to the main hydrocarbyl chain, such as $C_6H_4$—CH=, $C_6H_3$(R)—CH=, or $C_6H_4$—C(R)=, where R can be ($C_1$-$C_4$)alkyl or substituted ($C_1$-$C_4$)alkyl.

Another specific compound is of the formula (I) wherein $R^1$ can be saturated or unsaturated —($C_2$-$C_6$)alkylene-, —$Ar$—, or ($C_1$-$C_4$)alkyl substituted —Ar—; $R^2$ can be saturated or unsaturated —($C_1$-$C_6$)alkyl; and X can be halo.

Another specific compound is of the formula (I) wherein $R^1$ can be saturated or unsaturated —($C_2$-$C_6$)alkylene-, —$C_6H_5$—, or ($C_1$-$C_4$)alkyl substituted —$C_6H_5$—; $R^2$ can be saturated or unsaturated —($C_1$-$C_3$)alkyl; and X can be chloro.

Another specific compound is of the formula (I) wherein $R^1$ can be propyl —$CH_2$—$CH_2$—$CH_2$— or —$C_6H_5$—; $R^2$ can be —$CH_3$; and X can be chloro.

Another specific compound is of the formula (I) wherein $R^1$ can be undecyl —$(CH_2)_{11}$—; $R^2$ can be —Me, Et, Pr, Bu, i-Bu, s-Bu, or t-Bu; and X can be chloro and bromo.

A specific compound of the formula (I) is trichloro(3-(trimethoxysilyl)propyl)silane of the formula $(CH_3O)_3Si$—$CH_2$—$CH_2$—$CH_2$—$SiCl_3$

Another specific compound of the formula (I) is trichloro (11-(trimethoxysilyl)undecyl)silane of the formula $(CH_3O)_3Si$—$(CH_2)_{11}$—$SiCl_3$

Another specific compound of the formula (I) is trichloro (4-(trimethoxysilyl)phenyl)silane of the formula $(CH_3O)_3Si$—$C_6H_5$—$SiCl_3$ Another specific compound of the formula (I) is tribromo (4-((trimethoxysilyl)methyl)benzyl)silane of the formula $(CH_3O)_3Si$—$CH_2$—$C_6H_5$—$CH_2$—$SiBr_3$

Another specific compound of the formula (I) is tri-tert-butoxy(4-((trichlorosilyl)methyl)benzyl)silane of the formula (t-BuO)$_3$Si—$CH_2$—$C_6H_5$—$CH_2$—$SiCl_3$

Another specific compound of the formula (I) includes an $R^1$ of bis(4,4'-silane substituted-2,2'bipyridine) of the formula (t-BuO)$_3$Si-(4,4'-substituted-2,2'Bipy)-SiCl$_3$

Another specific compound of the disclosure incorporates one or more mono or bis(silane substituted-2,2'bipyridine) ligands and optionally a coordinating metal such as Ru(II), such as the photoactive dye cis-(NCS)$_2$bis(4,4'-dicarboxy-2,2'bipyridine)-ruthenium(II), for example of the formula below and like permutations thereof -continued The abovementioned specific compounds of the formula (I), and like compounds of the disclosure, can include a salt or salts thereof.

"$(C_1-C_4)$alkyl substituted" refers to having a "$(C_1-C_4)$alkyl substituent attached to an alkyl, aromatic, or heteroaromatic portion of the hydrocarbyl moiety $R^1$, having a $(C_1-C_4)$alkyl substituent attached to the substituents attached to an alkyl, aromatic, or heteroaromatic portion of the hydrocarbon moiety, or both. Thus, a $(C_1-C_4)$alkyl substituted —CH$_2$—C$_6$H$_4$—CH$_2$—, can be, for example, —CH$_2$—C$_6$H$_4$—CH$_2$— having one or more $(C_1-C_4)$alkyl substituent attached to the —C$_6$H$_4$—, one or more $(C_1-C_4)$alkyl substituent attached to either or both of the —CH$_2$— substituents, or both, such as —CH$_2$—(3-Et—C$_6$H$_3$)—CH$_2$—, —CH(Et)—C$_6$H$_4$—CH(Et)—, —CH(Et)—(3-Et—C$_6$H$_3$)—CH(Et)—, and like substituent and substitution patterns.

"1,4-Substituted," "para-substituted," or like prefixes refer to the substitution pattern of intra-chain or spacer backbone substituents on an aromatic or heteroaromatic portion of the hydrocarbon core. Thus, for example, "1,4-substituted —CH$_2$—CH$_2$—C$_6$H$_4$—CH$_2$—CH$_2$—" or simply "1,4-(-CH$_2$—CH$_2$—C$_6$H$_4$—CH$_2$—CH$_2$—)" refer to a para-substituted version of a diethylenyl phenyl hydrocarbon moiety.

"Hydrocarbon," "hydrocarbyl" and like terms, in the context of the asymmetric bis-silane compounds of the disclosure, refer to divalent —$R^1$-moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alky substituted heteroaryl hydrocarbons, alkoxy substituted heteroaryl hydrocarbons, and like hydrocarbon moieties, and as illustrated herein. In embodiments, the hydrocarbon of the asymmetric bis-silane compound can be selected to be the same, similar to, or at least chemically or physically compatible with those hydrocarbons, if any, contained in the substrate, such as an organic polymer such as an insulating, semiconducting, or conducting polymer or copolymer, an inorganic polymer such as a glass, an organic-inorganic hybrid polymer such as a organo substituted polysiloxane, or combinations thereof.

Bis-silane compounds of the disclosure, such as the abovementioned compounds of formula (I), can be prepared as described and illustrated herein, for example in the scheme below, by procedures analogous thereto, or by many different procedures, including partial or related procedures in the mentioned publications or patents. All of the variables used in the scheme(s) are as defined below or elsewhere herein.

The divalent hydrocarbon spacer unit can generally provide the resulting metal oxide composition having the surface bound siloxane with distinctive sites, pores, cavities, or the like surface structures, having high surface areas. The dimensions and chemical character of the resulting composite particle ensemble and their surface properties can be a priori engineered or readily altered post hoc by, for example, molecular modeling of geometries, surface energies, and like functional properties of possible or desired surface structures.

Other conditions suitable for formation and modification of the compounds, oligomers, copolymers, or like products of the disclosure, from a variety of starting materials or intermediates, as illustrated herein are known. For example, see Feiser and Feiser, "Reagents for Organic Synthesis", Vol. 1, et seq., 1967; March, J. "Advanced Organic Chemistry," John Wiley & Sons, $4^{th}$ ed. 1992; House, H. O., "Modem Synthetic Reactions," $2^{nd}$ ed., W. A. Benjamin, New York, 1972; and Larock, R. C., "Comprehensive Organic Transformations," $2^{nd}$ ed., 1999, Wiley-VCH Publishers, New York, the entireties of which are incorporated by reference herein.

The starting materials employed in the synthetic methods described herein are commercially available, have been reported in the scientific literature, or can be prepared from readily available starting materials using procedures known in the field. It may be desirable to optionally use a protecting group during all or portions of the above described or alternative synthetic procedures. Such protecting groups and methods for their introduction and removal are well known in the art. See Greene, T. W.; Wutz, P. G. M. "Protecting Groups In Organic Synthesis," 2.sup.nd ed., 1991, New York, John Wiley & Sons, Inc.

The bireactive bis-silane compounds, bis-silane metal oxide compositions, or bis-silane metal oxide substrate combinations, and devices of the present disclosure can be useful in other applications, for example, an organosilicone coating, a conversion coating, a passivating coating, a conditioning coating as used for example in gas or liquid chromatography, a coupling agent (e.g., see Pludemann, *Silane Coupling Agents*, (1982)), a surface modifier, a silicone elastomer or like rubber applications, such as articles or devices, and like applications.

One application of the materials and methods of the disclosure is the manufacture of solar cells or like devices. In a reported process (O'Regan, B.; Grätzel, M., *Nature,* 1991, 353, 737-740), $TiO_2$ particle layers were formed on a conductor modified glass substrate and subsequently treated in a high temperature, pseudo-sintering process to form a porous $TiO_2$ particle layer. However, titania is not readily sintered without loss of particle integrity since it changes phase, for example, from anatase to rutile, at temperatures below those needed to sinter and such phase transitions can cause a dramatic and detrimental reduction in particle film surface area. The reported process uses high temperatures (e.g., >300° C. such as 450° C. and above). This and other high temperature sintering processes are challenged by and are incompatible with potentially attractive alternative particulate and substrate materials, including many organic substrates, due to the instability of the alternative materials at high temperatures.

In embodiments the disclosure provides a photovoltaic device comprising: a substrate that reacts with and supports the reaction product, the substrate comprising at least one of a glass, a polymer, a ceramic, a ceramer, a composite, and like materials, or combinations thereof; and an optional photosensitizer material. The photosensitizer material can be, for example, a photosensitizer, a dye, a pigment, or combinations thereof. In embodiments one suitable dye is, for example, cis-$(NCS)_2$bis(4,4'-dicarboxy-2,2'bipyridine)-ruthenium(II) (See Sommeling et al., 2000). In embodiments, a dye or like photoactive molecule can be incorporated into the structure of the asymmetric bis-silane, such as illustrated herein.

In embodiments the disclosure provides a method of making the abovementioned photovoltaic device comprising: contacting a compound of formula (I) with a metal oxide particle; coating the resulting suspension on a substrate to form a film on the substrate; and heating the resulting coated substrate to form a substrate-film composite. In embodiments, the preparative methods for device fabrication can also be accomplished with a composition comprising the reaction product of a compound of formula (I) and a metal oxide particle. The preparative method can further comprise a substrate that reacts with and supports the reaction product, and the substrate can comprise, for example, at least one of a glass, a polymer, a ceramic, a ceramer, a composite, and like materials, or combinations thereof. In embodiments, heating the resulting coated substrate to form a substrate-film composite can be accomplished at, for example, at or below about 100° C., such as from about 20° C. to about 100° C., from about 30° C. to about 100° C., from about 40° C. to about 100° C., and from about 50° C. to about 100° C. The method can optionally include contacting the resulting substrate-film composite with a photosensitizer, and assembling the resulting composite with a photosensitizer with a second conductive substrate such as having a metal film, for example, platinum or like metals supported on glass or like substrate. As an example of a dye-sensitized solar cell on a flexible substrate, see Sommeling, et al., "*Flexible dye-sensitized nanocrystalline $TiO_2$ solar cells,*" ECN-RX-00-020; May, 2000; 5 pages; Presented at 16th European Photovoltaic Solar Energy Conference and Exhibition, Glasgow, Scotland, 1-5 May, 2000. For other examples of a solar cells based on sol-gel films see M. Grätzel, "Solar Cells Based on Sol-Gel Films" Chapter 14, Vol III: Applications of Sol-Gel Technology; S. Sakka ed., Kluwer Academic Publishers, Boston, 2004.

In embodiments the disclosure provides an electrochromic device comprising: a substrate that reacts with and supports the reaction product, the substrate comprising at least one of a glass, a polymer, a ceramic, a ceramer, a composite, or like materials, and combinations thereof; and an optional electrochromic material. The electrochromic material can be, for example, a dye, a pigment, or similar material, and combinations thereof which material changes it's light absorption properties upon reduction and/or oxidation by one or more electrons.

In embodiments the disclosure provides a photocatalytic device comprising contacting a compound of formula (I) with a metal oxide particle with reactive surface; coating the resulting suspension on a substrate to form a film on the substrate; and heating the resulting coated substrate to form a substrate-film composite. The substrate may optionally include a sensitizer and a device that directs reactant streams to the surface. The sensitizer may be a dye which can absorb light and activate the reactive material by injecting an electron into the catalyst, thereby increasing the reaction rate compared to the photactivation possible with the dye alone. The substrate may also be conductive and allow a voltage to be applied to the films to further enhance reactivity. The device must direct the reactants to the reactive surface, and remove the products from the reactive surface.

In embodiments the disclosure provides a method of making a photoelectrochemical device comprising: contacting a compound of formula (I) with a metal oxide particle; coating the resulting suspension on a substrate to form a film on the substrate; and heating the resulting coated substrate to form a substrate-film composite. The method can optionally include contacting the resulting substrate-film composite with a photosensitizer to enhance the optical spectrum that is absorbed. The device further comprises assembling the resulting composite as an electrode in combination with a counter electrode and electrolyte to achieve the ability to drive a chemical reaction with the photoelectric power derived by the substrate from composite.

In embodiments the disclosure provides devices made from the conductive particle films of the disclosure which are relatively inexpensive, easier to process, lighter in weight, easier to handle and process, more energy efficient to produce, optionally flexible, and like aspects.

In embodiments, the disclosure provides an asymmetric organo bis-silane compound having a central organic moiety and two silane groups having different reactivity. Each of the silane groups can react with particles and with surfaces exhibiting nucleophilic functionality such that a covalent bond is formed. In embodiments, the reactive silane groups have differential reactivity with respect to nucleophiles such that one group has significantly slower reaction kinetics compared to the other group with respect to nucleophilic coupling reactions of the silane to particle surfaces and to substrate surfaces. This differential reactivity allows a particle to quickly react with one silane reactive group without significant reaction at the other group. The second less reactive silane group can then react with another nearby particle or a nearby substrate surface to bind the particles together and hold the particles to the substrate.

In embodiments, the disclosure provides a method of using the bireactive silane compounds to form thin layers or films of particles that enhance the proximal contact of the particles. The resulting layers can be prepared at lower temperatures and enable the formation of particle films or particle layers on substrates that are typically labile at high temperatures such as polymers.

In embodiments, the disclosure provides a photovoltaic device including a thin layer of semiconductor metal oxide particles of, for example, silica, silicates, borosilicate, phosphosilicate, silicon nitride, silicon oxynitride, zinc sulfide, tantalum oxide, titania, titanates, alumina, aluminates, tin, tin oxide, tungsten, iron, and like oxides or mixed oxides, or combinations thereof, made in combination with the bireactive silane compound or like compounds, at lower temperatures (relative to temperatures typically used for conventional metal oxide particle adhesion), which device can deliver enhanced photo-efficiency by virtue of the proximal contact of its particles. The disclosed process can be accomplished at relatively low temperatures and on lower cost substrates. The disclosed process can provide significant cost and device performance improvements over those costs and devices that are fabricated at either high or low temperatures but without the bireactive silane of the disclosure.

Although not wanting to be limited by theory the following aspects are believed to be important considerations in the selection of materials and the robustness of the resulting devices. The LUMO of the dye should be at or above the level of the conduction band of the metal oxide or the mixed metal oxide particle film. The redox potential of the electrolyte should be at or above the HOMO level of the dye. The HOMO of the dye should be above the valence band of the metal oxide or the mixed metal oxide film. The counter electrode should be capable of injecting electrons into the redox electrolyte. The conducting substrate, such as the FTO, should be capable of accepting electrons from the metal oxide or the mixed metal oxide film.

In embodiments, the bireactive silane compound of the disclosure can produce particulate layers and films which have neighboring particles held in relatively close proximity to each other. The close and controlled proximity of neighboring particles allows for nearly crystalline contact in a film. The particulate layers or films can be readily prepared with mild heating, such as at or below about 100° C., to cause the particles to become sufficiently attached to adjacent particles and to a substrate to be useful in the fabrication of various devices. Use of the materials and processes of the disclosure avoids the cost and harshness of heating to high temperatures, that is, for example, greater than about 150 to about 300° C., such as with titania particles approaching about 500° C. In embodiments, the bireactive silane of the disclosure can be used to form layers or films of metal oxide particles having sufficient particle-particle cohesion and to substrates having sufficient adhesion for device fabrication without heating, for example, above about 100° C. This reduction in processing temperature permits the use of lower cost substrates such as polymers. At these lower temperatures most organic materials remain quite stable, while at 500° C. few, if any, organic materials are stable. This reduced process temperature enables the combination of various organic materials into devices at the film formation stage, the use of various organic materials for the substrate, or both. The bireactive silane and film forming process of the disclosure eliminate high processing temperatures and reduce energy costs.

The ability to bond particles together in close proximity can also enable a transition from discrete particle properties to continuous film properties. In embodiments, a nanocrystalline titania film processed in accord with the disclosed method can perform as a wide band-gap semiconductor. In embodiments, a construct known as a dye sensitized solar cell, such as a dye decorated titania film, can accept electrons injected from an organic dye sensitizer, and conduct the electron to a transparent conducting oxide surface (e.g., fluorinated tin oxide (FTO)), from which electrical energy can be harvested. While not limited by theory the titania particles or like particles, should have sufficient contact with adjacent or proximate titania particles that electrons generated on an outer particle are transported to proximate particles until the electron reaches the transparent conducting oxide layer. In the art this has typically been accomplished by partially sintering a nanocrystalline titania coating at about 450° C. By using the bireactive silane compounds of the disclosure as a particle-to-particle adhesive during the film formation or deposition of titania nanoparticles from a slurry, nanocrystalline films can be readily prepared and without high temperature sintering.

The resulting nanocrystalline films can have photovoltaic performance that approaches and may exceed the performance of high temperature sintered layers obtained by conventional processes. That good electrical conductivity could be achieved without forming crystallographic contact between particles was a surprising result and suggests that the proximal contact in these nanocrystalline films may be significantly different compared to non-adhered films. In embodiments it was found that the photovoltaic efficiency of the stitched particle films of the disclosure were comparable, such as from about 1.5 compared to about 2.0, for sintered particle films.

Scheme 1 below shows a synthetic route to a bireactive silane compound of formula (I) having the specific formula trimethoxysilylpropyltrichlorosilane 1, it's selective reaction with titania particles (gray spheres not to scale) or like metal oxide particles, and the subsequent formation of a cross-linked hybrid titania particulate film or particle layer on a substrate. The particulate film or layer can be comprised of one or more courses or layers of particles, for example, a single layer or multiple layers of linked particles. In embodiments, trimethoxysilylpropyltrichlorosilane 1 reacts with titania particles suspended in an inert solvent forming covalent bonds through the reaction of the trichlorosilyl moieties. Thus reacted, this suspension of titania particles, with unreacted trimethoxysilyl groups appended, may be deposited as a thin film on a substrate surface having nucleophilic sites, such as a glass, fluorinated tin oxide, a polymer, and like substrates or combinations thereof. The trimethoxysilyl moieties will also react, although much more slowly, with the titania particles and with the substrate surface. The reaction may be accelerated by heating the thin layer of particles on the substrate to a moderate temperature, for example, below about 200° C., such as about 100° C. is sufficient to complete the reaction in under about 1 hour. The reaction of the trimethoxysilyl groups causes the particles to cross-link or conjoin, and link to the substrate, such that the film integrity remains without the need to sinter the particles at high temperatures such as where organic materials may be unstable.

Scheme 2. Synthesis of p-trimethoxysilylphenyltrichlorosilane 2.

These and other syntheses are described herein and further exemplified in the working examples.

Unsymmetrical Bi-Functional Silanes and Methods for Particle Coupling

The asymmetrical bi-functional or bireactive silanes of the disclosure of the formula $(R^2O)_3Si-R^1-SiX_3$ have differential reactivity which permits the silanes to be selectively reacted with the surface of a metal oxide particle (P) in a stepwise fashion to afford a first intermediate product and a second product. In the first intermediate product the more reactive of the silane's two functional groups $-SiX_3$ reacts partially or completely with the surface of the metal oxide particle to form a metal oxide particle having one end of the bi-functional silane attached to the particle surface, for example, of the formula $(R^2O)_3Si-R^1-SiX_2-O-P$. Subsequent mild heating affords the second product where the unreacted second end of the surface attached silane's functional group of the formula $(R^2O)_3Si-$ reacts with the surface of one or more adjacent similarly functionalized metal oxide particle (P') to produce a coupled or cross-linked product or multiples thereof of the formula $P'-O-(R^2O)_m-Si-R^1-SiX_n-O-P$ where m and n can be from 1 to 2.

In embodiments, an alternative process comprises contacting the abovementioned first or intermediate product having one of the silane's two functional groups bonded to the surface of the metal oxide particle, for example, of the formula $(R^2O)_3Si-R^1-SiX_2-O-P$ with a fresh or unreacted metal oxide particle (P) to produce a coupled or cross-linked product or multiples thereof, for example, of the formula $P-O-(R^2O)_m-Si-R^1-SiX_n-O-P$.

Scheme 1. Synthesis of a cross-linked hybrid titania particle film on a substrate.

Scheme 2 below shows the synthesis of another exemplary bireactive silane for the formation of films of the disclosure having the specific formula of p-trimethoxysilylphenyltrichlorosilane 2.

In either of the above first or the alternative second process, a particle ensemble results having metal oxide particles that are cross-linked or bridged with a bis-silane spacer of the formula of, for example, —O—Si—$R^1$—Si—O—. Depending upon the relative ratio of asymmetric bi-functional silane reactant to available reactive functional groups on the surface of the metal oxide particles, the resulting particle ensemble may still have unreacted silanes functional groups, such as —O—$(R^2O)_m$—Si—$R^1$—$SiX_n$—O— where m and n can be from 1 to 2, that can react further with, for example, a suitable substrate, such as a glass, a polymer, a ceramic, a ceramer, a composite, and like materials, or combinations thereof, to attach or link the cross-linked particle ensemble to the substrate. In embodiments, the particle ensemble having unreacted silane groups can be reacted with an added second but different metal oxide particle, such as a silicate, and like metal oxide particles or mixed metal oxide particles, such as a borosilicate, and like mixed metal oxide particles.

In embodiments, the reaction of the silane's second functional with adjacent or added metal oxide particles can be accomplished in the presence of a substrate to simultaneously achieve particle cross-linking and ensemble formation and to attach the cross-linked particle ensemble to the substrate with a bis-silane unit of the formula ≡Si—$R^1$—Si≡.

In embodiment, relative proportions of the reactants can be varied depending on properties desired in the product films, such as film thickness, porosity, density, surface area, photosensitivity and like properties. Applications such as dye sensitized photovoltaic cells can bond sensitizers to the inorganic film surface, and in embodiments distribute sensitizer over as much surface area as possible to achieve a high absorption coefficient, and low recombination rates. In embodiments, as more bireactive silane bonding agent is added, the proximate bonding of particles is expected to increase, but at the expense of available surface area on the particles. Each bireactive silane $A_3Si$—$R^1$—$SiB_3$, such as 1 or 2, can occupy as many as 6 surface sites, but due to potential geometrical mismatch effects the silane is more likely to occupy, for example, 4 surface sites and may occupy as few as 2 surface sites on a high surface area metal oxide particle. There are approximately 5 surface hydroxyls on each square nanometer ($nm^2$) on the titania surface so that 3 grams of titania has about $1.5 \times 10^{20}$ surface hydroxyls (Ti—OH). If the bireactive bonding agent is assumed to consume 4 hydroxyls then 7.4 microliters of trimethoxysilylpropyltrichlorosilane 1 (30 micromole) will occupy about 10% of the available surface sites. Optimal performance or properties can be achieved in various applications with higher or lower coverage.

Other similar bireactive silanes in which the core hydrocarbyl group ($R^1$) or like groups is replaced or substituted by a different group, can be prepared by similar methods. Triethoxysilyl-ethyltrichlorosilane, its preparation, and its use in elucidating metal colloid catalyzed hydrosilylation mechanisms has been reported (Lewis, L. N., *J. Am. Chem. Soc.*, 1990, 112, 5998-6004). In embodiments of the present disclosure the synthesis of bireactive silanes having longer carbon chains in the middle of the molecule are accessible and the disclosed coupling and device forming processes are also expected to work with these compounds. However, if the chains become too long and sufficiently flexible, the particle cross-linking efficiency may be reduced due to the increased likelihood of reaction of the slower reacting trialkoxy group with the same particle (intraparticle reaction) that the trihalosilyl group reacted with. The extra bulk of larger organic radicals may also take up space at the surface of the particles, thus blocking access and reducing efficiency for subsequent reactions of the films produced. It should also be possible to produce differentially reactive functional materials having a single carbon or no bridging carbon atoms, substituted or unsubstituted, between the bireactive silane groups of the formula $A_3Si$—$SiB_3$ or $A_3Si$—$CR_2$—$SiB_3$ where each R is for example independently H or alkyl. It may also be possible for the disclosed process to work with a mononuclear bireactive silane of the formula $A_2SiB_2$ where $R^1$ is nil or a single bond, such as dialkoxydichlorosilane, $(RO)_2SiCl_2$. However, this type of bireactive silane may lead to poor film formation due to the limited reach of the molecule and thus the need for precise alignment of reactive groups on adjacent particles or surfaces. The multi-carbon bireactive silane compounds of the disclosure may have some chain flexibility and may accommodate slight misalignment with particle reactive sites. The asymmetric groups of the bireactive silane need not be trichloro- and trialkoxysilanes. Instead they may simply need to have differential reactivity with nucleophiles and have the ability to form covalent bonds with particle and substrate nucleophilic groups. In embodiments, one or two of the chlorines, alkoxy groups, or both, may be replaced with other groups that are not reactive groups, such as alkyl or aryl. The resulting compound(s) are expected to function in a similar bireactive manner. However, compounds having fewer than 6 reactive groups are expected to be less efficient particle cross-linkers and substrate couplers.

In embodiments, the asymmetric bireactive groups need not both be silyl groups nor silyl groups at all. Any two differentially reactive functional groups that are capable of selectively forming covalent bonds with nucleophiles in a stepwise fashion as illustrated herein are expected to be similarly useful. Other functional groups may be used where their synthesis is practicable, for example, bireactive stannates of the formula $A_3Sn$—$R^1$—$SnB_3$, mixed bis-acid halides of the formula A—(C═O)—$R^1$—(C═O)—B where A is more or less (but not the same) reactive than B, and like differentially reactive functional groups and mixed bireactive compounds such as $A_3Sn$—$R^1$—$SiB_3$. The effectiveness of these materials may depend on the degree of differentiation between the reactivity of the groups and the degree to which the structure accommodates the requirements of the particles.

Figure 1:
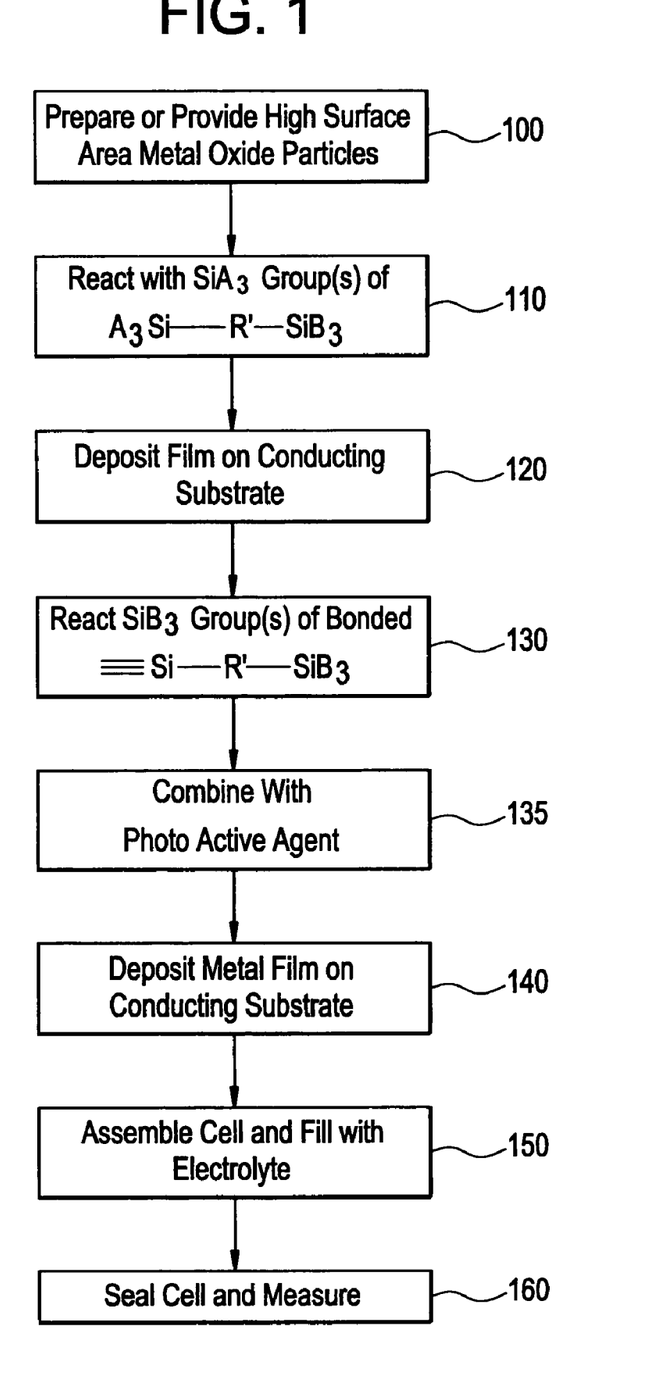
FIG. 1 shows an exemplary flow chart of a lower temperature process for preparing a solar cell device using the bireactive silanes in embodiments of the disclosure.

Referring to the Figures, FIG. 1 shows a flow chart of a lower temperature process for preparing, for example, solar cell and like devices using a bireactive silane bonding material and particulate metal oxides of the disclosure. Films having high surface area particles, such as titanium oxide particles, were prepared and bonded together with, for example, either the propylsilane 1 or the phenylsilane 2. In one example, approximately 10% of the titanium oxide particle surface is covered with Ti—O—Si bonds forming the adhesive link between proximate particles.

The disclosed process route and the comparative process (O'Regan, ibid.) differed in the method by which particles within the film were brought into a conductive bonded state. The comparative process used a conventional process with a high temperature sintering step to form crystalline necks between adjacent particles. Such high temperatures preclude the use of substrates having lower thermal stability, such as polymers. The inventive process route of the disclosure also used a much lower temperature (i.e., at or below about 100° C.) to react the second less reactive silyl functional groups with adjacent particles.

Thus, for example as summarized in FIG. 1, high surface area metal oxide particles, such as $TiO_2$ nanoparticles or like particles, were prepared or provided (100) and controllably reacted with the more reactive portion (e.g., A groups) of a bireactive silane of formula (I) (110). The resulting film, comprised of a particulate film, was deposited on a suitably conducting substrate (120), such as a glass or an organic polymer having a conducting coating thereon, such as fluorinated tin oxide (FTO) or indium tin oxide (ITO) to form a "lower" conducting substrate. The substrate deposited particulate film was then heated, for example from about 50 to about 100° C., to react the residual unreacted or less reactive B groups of the particle bonded bis-silane (130) to join the particle film with the substrate. The resulting particle film and substrate were treated, such as for about several minutes to 24 hours, with a photoactive agent (135) such as a colorant, for example, a suitable dyestuff. Next a metal film such as platinum, or like substance, was deposited on a second conductive substrate (140) such as a glass or an organic polymer to form an "upper" conducting substrate. Modifying a known process (O'Regan, ibid.), a solar cell was constructed from various films using the materials and the process of the disclosure. A cell was assembled and the cell filled with electrolyte (150) by combining the first conductive substrate having a deposited metal film and the second conductive substrate having the deposited stitched particle film-conductive substrate bearing the photoactive agent. In an alternative approach to preparing the cell, the photoactive dye can be fixed on the particle film surface within the assembled cell by treating with a solution of the photoactive agent for a time, then emptying the cell, and then filling the cell with electrolyte (150). Finally, the cell was sealed and the electrical properties measured (160). Alternatively, the particle film can be dyed before or after the particle film combined with a substrate or is assembled into a cell.

In a comparative process (not shown) (O'Regan, ibid.), a cell was prepared with higher temperature sintering as follows: high surface area metal oxide particles, such as $TiO_2$ nanoparticles or like particles, were prepared or provided without a bireactive silane of formula (I). A particulate film of the high surface area particles was solution deposited on an FTO coated glass. The substrate deposited particulate film was then heated, for example from about 450° C., to sinter the particulate film and join the particle film with the substrate. Next a photoactive dye was fixed on the particle film surface. Thereafter a metal film such as platinum, or like substance, was deposited on the FTO coated glass. A cell was assembled by combining the resulting metal film deposited on the FTO coated glass with the dye fixed particle film. The cell was filled with electrolyte, the cell was sealed, and the electrical properties measured.

Figure 2A:
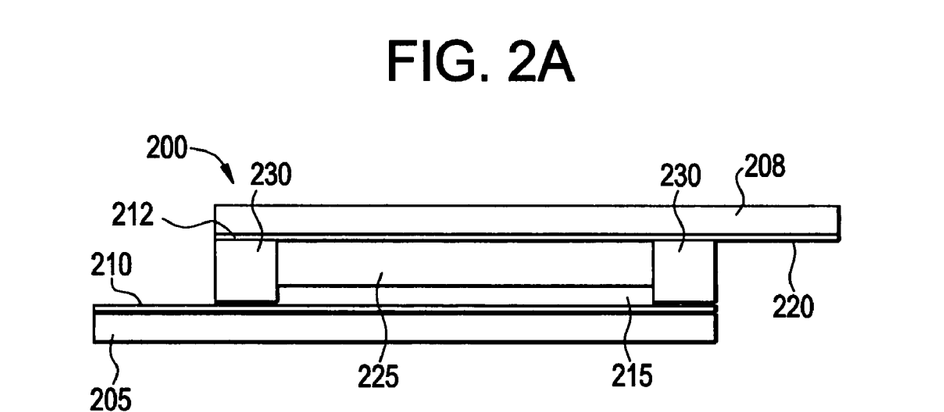
FIGS. 2A and 2B show a section and a plan view, respectively, of a photoactive device which incorporates a particle film formed with the bireactive silanes, in embodiments of the disclosure.
Figure 2B:
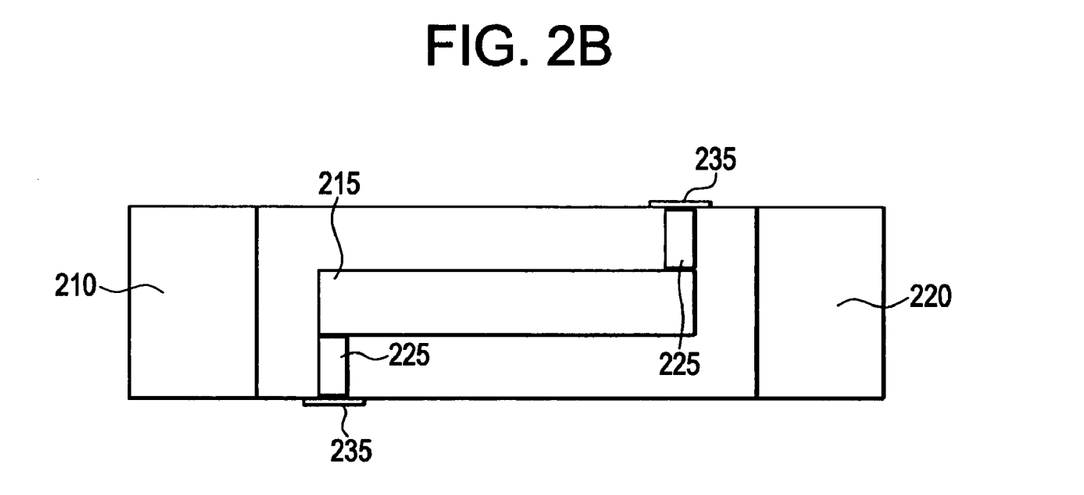

FIG. 2A shows a section view and FIG. 2B show its plan view of a photoactive device (200) having illustrative structural components, which device incorporates a particle film formed with the bireactive silanes of the disclosure. Thus, on a first substrate (205) is a transparent conducting oxide (TCO) coating (210) to form the "lower" conducting substrate. In embodiments, the TCO may be FTO, ITO, and like materials, or combinations thereof, having appropriate transparency and conductivity properties. A metallic coated layer (220), such as platinum, covers a second substrate (208) having an intermediate conductive layer (212), to form an "upper" conducting substrate. In embodiments, if the metallic coated layer (220) is sufficiently thick, so as to render the layer of sufficient conductivity, the intermediate conductive layer (212) is unnecessary and therefore optional. As a consequence of thickness, the metallic layer (220) may be rendered opaque. The metallic layer (220) may also be reflective. In embodiments, the first substrate (205) and second substrate (208) can be the same or different materials. Situated between these coated substrates is a dyed porous titania film (215) of the disclosure, in contact with the conductive coating (210) and an electrolyte (225). The electrolyte (225) is also in contact with the metallic coating (220). Seal gaskets (230) situated between the coated first (205) and second (208) substrates along with sealant material or members (235) shown FIG. 2B (not visible in FIG. 2A) provide a working cell.

Figure 3:
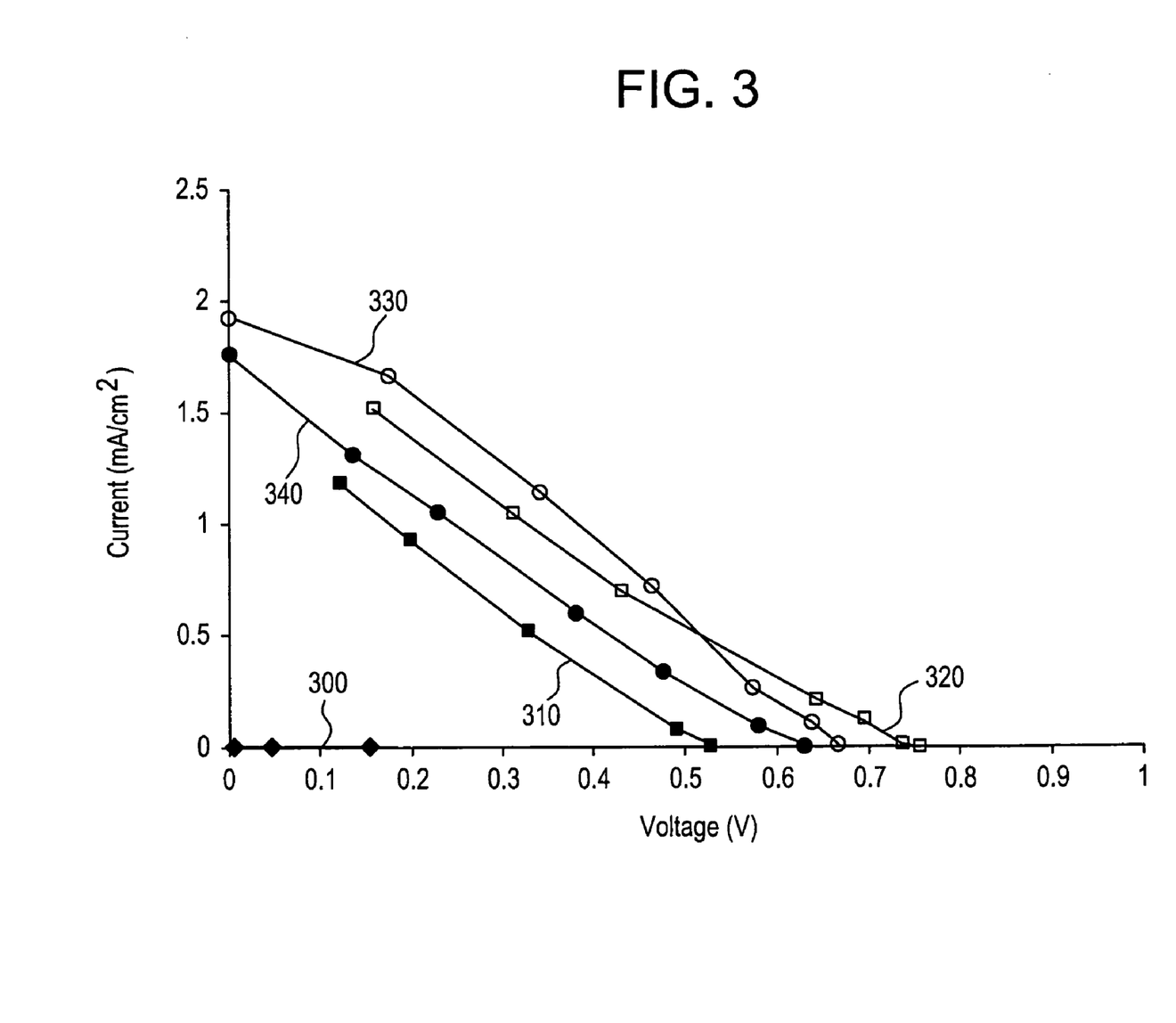
FIG. 3 shows actual and comparative current voltage (I-V) curves for solar cells prepared in embodiments of the disclosure.

FIG. 3 shows comparative and actual current voltage (I-V) curves for solar cells of the disclosure. A comparative or reference lower surface area unsintered Degussa P25 processed at lower temperature having no bis-silane is shown as curve (300). A comparative lower surface area sintered Degussa P25 having no bis-silane is shown as curve (310). A comparative higher surface area sintered Solaronix $TiO_2$ having no bis-silane is shown as curve (320). An actual lower surface area unsintered Degussa P25 processed at low temperature prepared with phenyl compound 2 bireactive silane bonding material is shown as curve (330), and for the propyl compound 1 bireactive silane bonding material is shown as curve (340).

Figure 4:
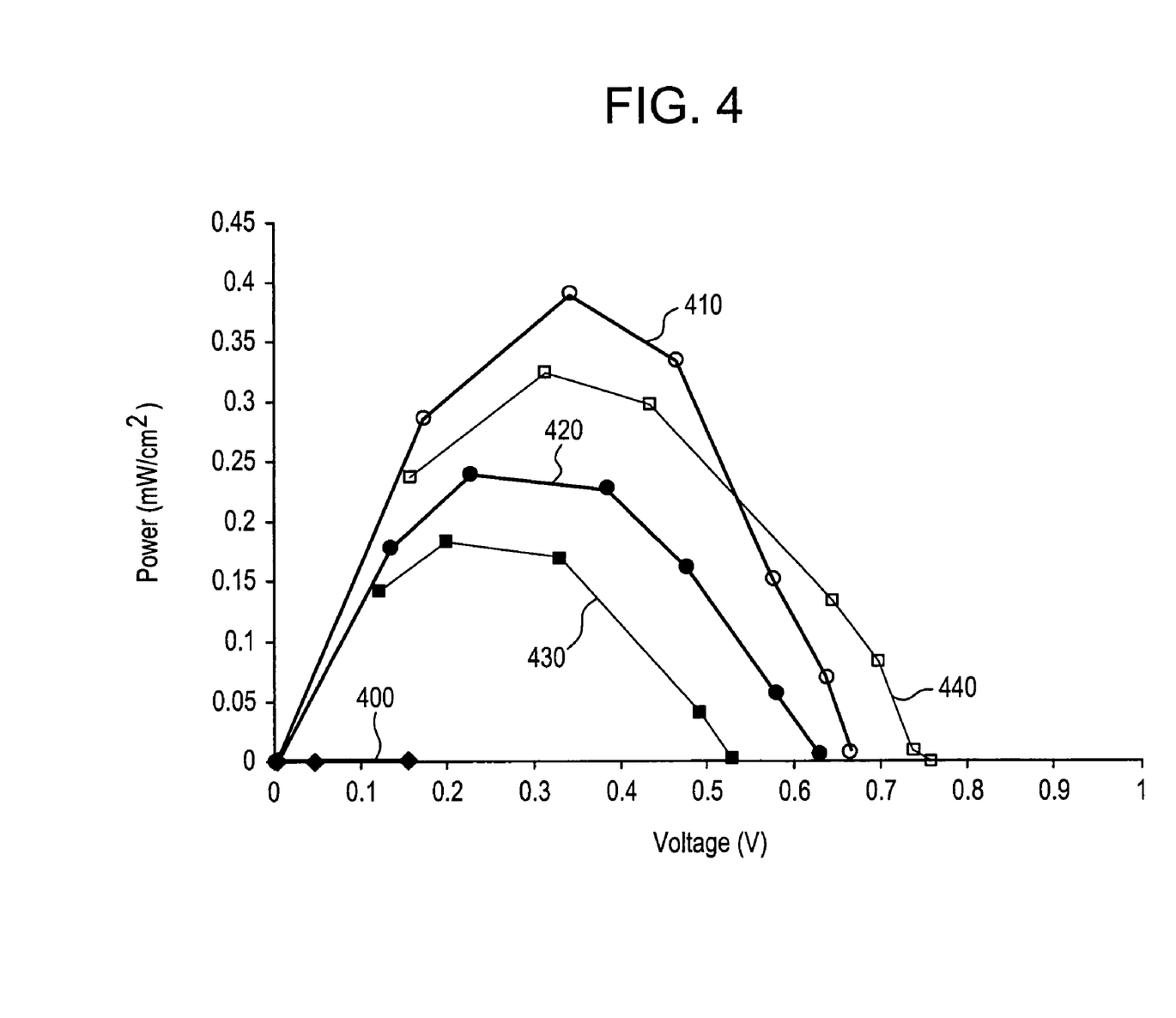
FIG. 4 shows actual and comparative power curves for solar cells prepared in embodiments of the disclosure.

FIG. 4 shows actual and comparative power curves for solar cells of the disclosure. A comparative or reference lower surface area unsintered Degussa P25 processed at lower temperature having no bis-silane is shown as curve (400). A comparative lower surface area sintered Degussa P25 having no bis-silane is shown as curve (430). A comparative higher surface area sintered Solaronix $TiO_2$ having no bis-silane is shown as curve (440). An actual lower surface area unsintered Degussa P25 processed at low temperature prepared with phenyl compound 2 bireactive silane bonding material is shown as curve (410), and for the propyl compound 1 bireactive silane bonding material is shown as curve (420).

Figure 5:
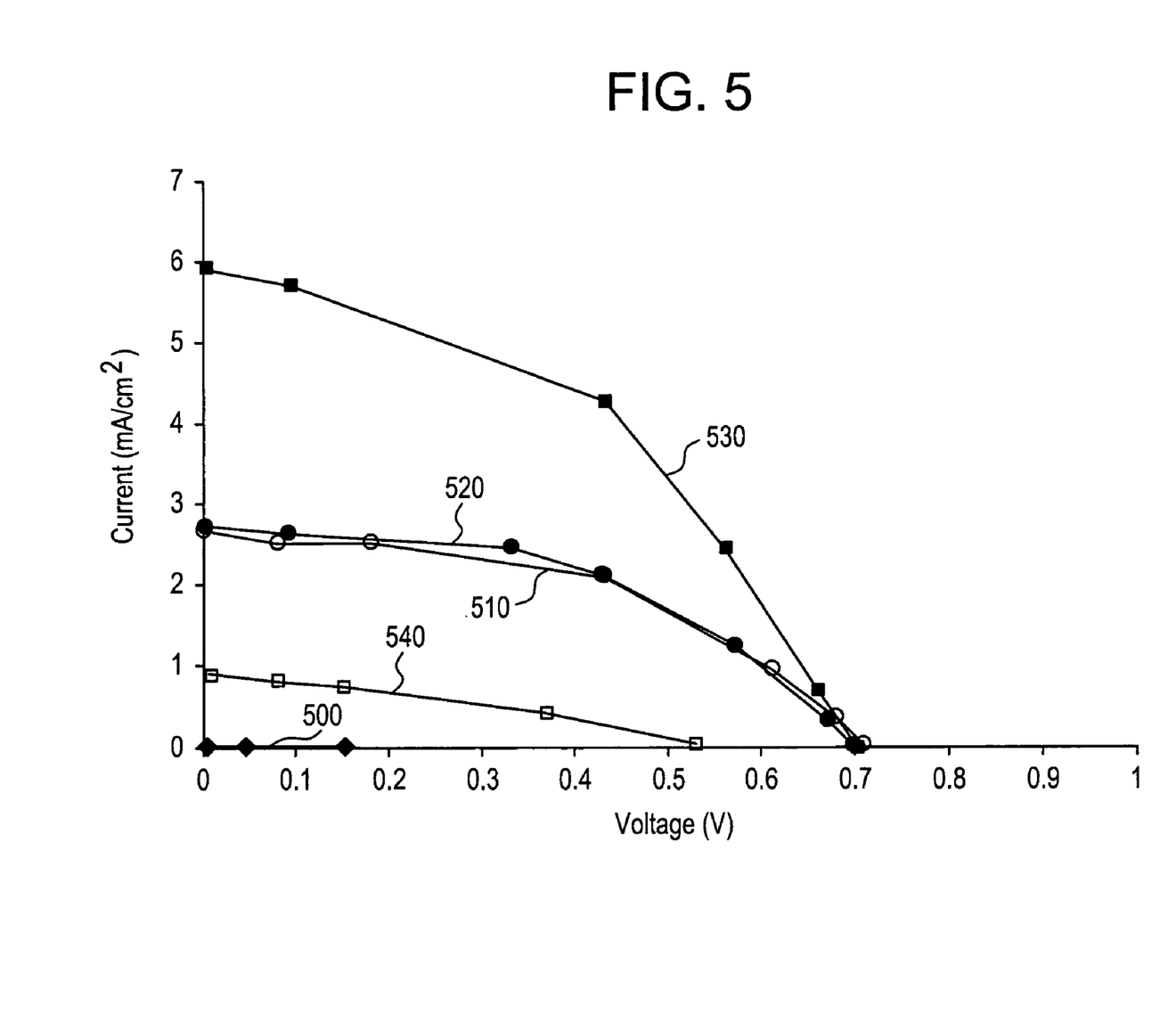
FIG. 5 shows additional actual and comparative current voltage (I-V) curves for solar cells prepared in embodiments of the disclosure.

FIG. 5 shows additional comparative and actual current voltage (I-V) curves for solar cells of the disclosure. A comparative or reference lower surface area unsintered Degussa P25 processed at lower temperature having no bis-silane is shown as curve (500). An actual lower surface area unsintered Degussa P25 processed at low temperature prepared with the propyl compound 1 bireactive silane bonding material on glass is shown as curve (510). An actual lower surface area unsintered Degussa P25 processed at low temperature prepared with the undecyl compound 3 bireactive silane bonding material is shown as curve (520). A comparative lower surface area sintered Degussa P25 having no bis-silane is shown as curve (530). An actual unsintered Degussa P25 processed at lower temperature having a propyl bridge ($R^1$) on plastic is shown as curve (540).

Figure 6:
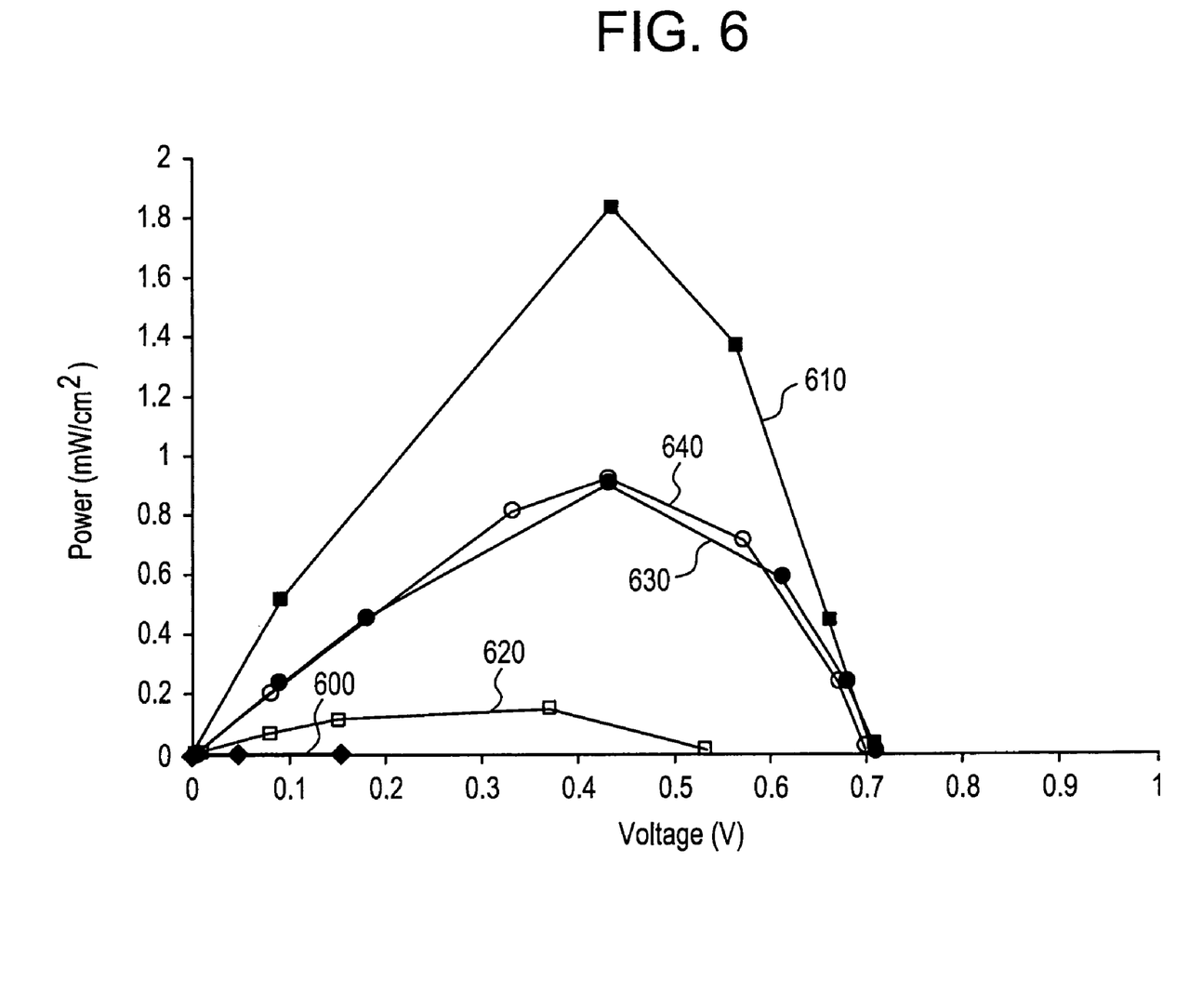
FIG. 6 shows additional actual and comparative power curves for solar cells prepared in embodiments of the disclosure.

FIG. 6 shows additional actual and comparative power curves for solar cells of the disclosure. A comparative or reference lower surface area unsintered Degussa P25 processed at lower temperature having no bis-silane is shown as curve (600). A comparative lower surface area sintered Degussa P25 having no bis-silane is shown as curve (610). An actual unsintered Degussa P25 processed at lower temperature having a propyl bridge ($R^1$) on plastic is shown as curve (620). An actual lower surface area unsintered Degussa P25 processed at low temperature prepared with the propyl compound 1 bireactive silane bonding material on glass is shown as curve (630). An actual lower surface area unsintered Degussa P25 processed at low temperature prepared with the undecyl compound 3 bireactive silane bonding material is shown as curve (640).

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

Example 1

PREPARATION OF BIREACTIVE SILANE 1. Trimethoxysilylpropyltrichlorosilane, 1, was prepared as follows. A 2-necked round bottom flask was pump-filled with nitrogen, the main neck having a fitted reflux condenser and the other neck a septum. A solution of allyltrimethoxysilane (5 mL, 29.7 mmol) in diethyl ether (10 mL) was added followed by trichlorosilane (6 mL, 59.4 mmol). While stirring under a positive pressure of nitrogen, the septum was quickly removed and chloroplatinic acid (2 mg, 4.88 micromol) was added, and the septum replaced. The mixture was then stirred 16 hours at 20° C. Next, the diethyl ether and remaining trichlorosilane were removed by evaporation under reduced pressure. The residual liquid product was purified by distillation under reduced pressure, bp 32° C. at 0.26 mm Hg, to afford a colorless liquid. $^1$H and $^{13}$C NMR analysis confirmed the structure of the trichlorosilane 1, which are in agreement with its predicted spectra.

$\delta_H$ (CDCl$_3$, 300 MHz) 0.96 (2H, t, J 8.0, b), 1.24 (2H, t, J 7.8, d) 1.62-1.85 (2H, m, c), 3.60 (9H, s, a); $\delta_C$ (CDCl$_3$, 75 MHz) 15.8 (1C, b), 17.5 (1C, c), 22.1 (1C, d), 51.4 (3C, a).

Example 2

PREPARATION OF BIREACTIVE SILANE 2. p-Trimethoxysilylphenyltrichlorosilane 2, was prepared as follows. Magnesium turnings (1 g, 41.1 mmol) were stirred in dry tetrahydrofuran (40 mL) and a single iodine crystal was added. Bromophenyltrimethoxysilane (10 g, 36.1 mmol) was added and the suspension was stirred at 50° C. for 3 hours. The suspension was cooled to 20° C. and filtered into a dropping funnel. The solution was then added dropwise to a rapidly stirred solution of silicon tetrachloride (12.3 g, 72.4 mmol) in hexane (80 mL). Once addition was complete the suspension was stirred at 20° C. for 16 hours. The solvents and excess silicon tetrachloride were removed under reduced pressure and the product was purified by distillation under vacuum to afford a colorless liquid. This material was unstable in air and was used as produced. This material can be used as 1 or in combination with 1 to produce films of titania. $^1$H and $^{13}$C NMR analyses confirmed the structure of the trichlorosilane 2, which are in agreement with its predicted spectra.

$\delta_H$ (CDCl$_3$, 300 MHz) 3.62 (9H, s, a), 7.30-7.72 (4H, m, c, d); $\delta_C$ (CDCl$_3$, 75 MHz) 128.1 (2C, c), 130.6 (1C, b), 132.6 (2C, i), 134.7 (2C, d), 136.3 (1C, e).

Example 3

PREPARATION OF BIREACTIVE SILANE C$_{11}$ The 11-Trimethoxysilylundecenyltrichlorosilane 3, was prepared as follows. A 2-necked round bottom flask was pump-filled with nitrogen, the main neck having a connection to the nitrogen line and the other neck a septum. 10-Undecenyltrimethoxysilane (2.74 g, 10.0 mmol) was added with dry diethyl ether (20 mL) and stirred. Trichlorosilane (2.00 g, 14.8 mmol) was then added. While stirring under a positive pressure of nitrogen, the septum was quickly removed and chloroplatinic acid (1 mg, 2.4 micromol) was added, and the septum replaced. The mixture was then stirred for 48 hours at room temperature. The chloroplatinic acid catalyst was removed by filtration and the diethyl ether and remaining trichlorosilane were removed by evaporation under reduced pressure. The residual liquid product, a colorless liquid, was deemed pure enough (by NMR analysis) for use without further purification. $^1$H and $^{13}$C NMR analysis confirmed the structure of the trichlorosilane 3, which are in agreement with its predicted spectra.

$\delta_H$ (CDCl$_3$, 300 MHz) 0.86 (2H, t, J 8.1, b), 1.05-1.70 (20H, m, c-l), 3.61 (9H, s, a); $\delta_C$ (CDCl$_3$, 75 MHz) 14.4 (1C, b), 19.3, 22.6, 24.3, 29.1, 29.4, 29.5, 29.7, 31.7, 32.1, 32.6, (1C, b-l), 51.2 (3C, a).

Example 4

MIXED TITANIA-ALUMINA PARTICLE FILM FORMATION—PLASTIC SUBSTRATE Silane 1 of Example 1 was reacted with a suspension of titania particles in N-methylpyrolidinone (NMP). Thus, for example, Degussa P25 titania particles (50 g; surface area of 50 m$^2$/g) was combined with alumina grit (50 mg, average particle diameter 48 microns) and mixed well to evenly distribute the particles. The relatively large alumina particles were selected as a suitable insulator or spacer to effectively separate the electrodes and avoid shorting the assembled cell. A 2 g sample of this mixture was suspended in NMP (7.62 mL) also containing cetyltetramethylammoniumbromide (CTAB) (284 mg) and sonicated for 20 min. Trimethoxysilylpropyltrichlorosilane, 1, (4.9 microL) in NMP (0.5 mL) was then added and the mixture shaken vigorously for 2 min. An aliquot of the suspension was then placed on a indium tin oxide (ITO) coated plastic (Mylar®) substrate and spread into a thin (about 75 micrometers) film. This film was then heated from below on a hotplate set to about 100° C. for 1 hour, after which time the temperature was reduced to about 70° C. The film formed and bound to the substrate. The bound film can be further functionalized if desired with, for example, a photosensitive dye such as for making a solar cell device.

Example 5

PARTICLE FILM FORMATION—GLASS SUBSTRATE Silane 1 of Example 1 was reacted with a suspension of titania particles in acetonitrile. Thus, for example, trimethoxysilylpropyltrichlorosilane, 1, (7.4 microL) in acetonitrile (2 mL) was added to Degussa P25 titania particles (3 g; surface area of 50 m$^2$/g) in acetonitrile (15 mL). A further aliquot of acetonitrile (3 mL) was quickly added and the suspension shaken vigorously for 1 minute. The suspension was moderately shaken for 5 more minutes to aid dispersion of the particles. An aliquot of the suspension was then placed on a fluorinated tin oxide (FTO) coated glass substrate and spread into a thin (about 50 micrometers) film. This film was then heated from below on a hotplate set to about 100° C. for 1 hour, after which time the temperature was reduced to about 70° C. The film formed and bound to the substrate. The bound film can be further functionalized if desired with, for example, a photosensitive dye such as for making a solar cell device.

Example 6

$C_{11}$ Silane Particle film formation $C_{11}$ Silane of Example 3 was reacted with a suspension of titania particles in N-methylpyrolidinone (NMP). Thus, for example, a suspension of Degussa P25 titania particles (2 g; surface area of 50 m$^2$/g) in NMP (7.4 g) was sonicated for 20 min. Trimethoxysilylundecyltrichlorosilane 3 (6.9 microL) in NMP (1 mL) was then added and the mixture shaken vigorously for 2 min. An aliquot of the suspension was then placed on a fluorinated tin oxide (FTO) coated glass substrate and spread into a thin (about 40 micrometers) film. This film was then heated from below on a hotplate set to about 100° C. for 1 hour, after which time the temperature was reduced to about 70° C. The film formed and bound to the substrate. The bound film can be further functionalized if desired with, for example, a photosensitive dye such as for making a solar cell device.

Example 7

Dye Modified Film Formation And Solar cell device Fabrication After cooling the respective films cast in Examples 4 to 6 to 70° C., the resulting bis-silane bonded titania or mixed titania-alumina particle films were immersed in a solution of 20 mg of Ru535 dye dissolved in ethanol (100 mL), and allowed to soak overnight. The particle films adsorbed the dye. After rinsing with ethanol the films were a dark red color. The films were dried in a dry nitrogen stream for about 30 seconds, and then sealed to a counter-electrode assembly consisting of a platinum film deposited on fluorine doped tin oxide (FTO) on soda lime glass. A gap of about 20 to 100 micrometers was left between the two electrodes into which an electrolyte containing KI/I$_2$ was added. The gap was then sealed with epoxy.

Example 8

Solar cell device evaluation FIG. 3 shows current voltage (I-V) curves of the performance of solar cells made with, for example, actual and comparative materials as described above.

When illuminated with UV-visible light the cell generated electrical power. The cell was characterized by measuring the current and voltage across various loads to provide a current-voltage (I-V) curve as shown in FIG. 3. It is desirable for a cell to generate as much current as possible at each voltage so as to maximize the conversion of light to electrical energy.

FIG. 4 shows I-V (power) curves measured from 5 cells as described above. Two of these cells were prepared using the inventive route. Three cells were comparative or reference cells and do not use a bireactive silane coupling compound to bond the particles; two of these cells used the sintering process of the abovementioned comparative route, and one of these cells used a low temperature process similar to the inventive route, but without any bireactive silane coupling compound. Thus, two of the three non-inventive examples of solar cells were prepared by high temperature sintering to achieve proximate particle bonding. The third non-inventive cell was prepared from a high surface area titania slurry (obtained commercially from Solaronix), sintered to 450° C. for 30 minutes and its I-V results were plotted (50).

An optimized dispersion can provide for uniform coatings with little visible light scattering in the films. The second comparative cell was made using Degussa P25 titania powder slurried with polyethylene glycol as a binder in water. The visual quality of this film is similar to that obtained with the P25 powder with the bireactive silane coupling material. The film was also sintered at 450° C. for 30 minutes and its I-V results plotted. The third comparative cell was made with Degussa P25 in an acetonitrile/methanol solvent. The film was made and thermally treated in exactly the same way as the two inventive cells but without any of the bireactive silane coupling agent, that is, with only a 100° C. thermal treatment, and no high temperature sintering and its flatline I-V and power results plotted as (300) and (400). The visual quality of this film is similar to that obtained with the P25 powder with the bireactive silane coupling material. In embodiments, it is expected that better film thickness uniformity can lead to better light absorption and cell performance.

The I-V and power curves in FIGS. 3 and 4 show some surprising results. The two inventive cells plotted as curves (330) and (340) show very similar behaviors having, a maximum current of about 12 milliamps and maximum voltage of about 0.65 V. The films prepared with phenyl-bridged (330) coupling agent drives more current than the propyl-bridged (340) material, but this may be within the range of cell to cell variations. The inventive results are similar to that obtained for a high surface area sintered Solaronix films plotted as (320). The sintered Solaronix material (440) displays a higher voltage and intermediate current compared to the unsintered bireactive propyl silane 1 bonded material (420) but a lower voltage and intermediate current of unsintered bireactive phenyl silane 2 bonded material (410). Power in the phenyl-bridged silane bonded cell (410) however peaks at a significantly higher level.

A sintered version of the P25 titania free of a bis-silane gave lower values of open circuit voltage, short circuit photocurrent, and power than the bis-silane bonded cells. This direct comparison of cells made with the same titania material highlights how the bis-silane bonding process and bis-silane materials shows performance advantages approaching that obtained for traditional processing. Importantly, the non-sintered P25 cell made without any bireactive silane bonding material shows virtually no photoactivity (300). This observation further supports the surprising result of how a low temperature processed film can allow photoelectrons to flow through the film of proximally bonded titania particles. As an electron is injected into the titania layer it effectively shifts the Fermi level in the semiconductor into the conduction band. The natural bias in the cell tries to drive the electron from the semiconductor layer to the transparent conducting oxide layer underlying the titania film. The high energy electron can do work before it flows back into the electrolyte and reduces the sensitizer. If there is a high resistance in the circuit, such as non-contacting titania particles, then the electron flow is halted and current does not flow, for example, as is seen in the unsintered P25 with no bonding agent sample curve (300). The Ti—O—Si—R$^1$—Si—O—Ti chemistry that is believed to bond particles together is not expected to be particularly conductive based on first principles, yet the presence of small amounts properly bonded to metal particles enables substantial current flow. Although not limited by theory, the proximate contact of the particles either allows current to flow through these bis-silane bridges, or creates a close particle-to-particle alignment that promotes low resistivity electron flow.

These results demonstrate an example of the disclosed low temperature process using fine metal oxide powders where the films and cells prepared with a bis-silane compound performs significantly better than a high temperature sintered version of the cell. A parameter of considerable commercial interest in a photovoltaic product is the power that the device can deliver per unit cost. The photovoltaic device prepared by a low temperature process of the disclosure appears to provide significant power generation while permitting a selection of lower cost alternative substrates, for example, a polymer, a low temperature glass, a ceramer, a sol-gel, and like materials.

Example 9

Electrochromic Device Fabrication and Evaluation

TUNGSTEN TRIOXIDE PARTICLE FORMATION Tungsten trioxide particles of from about 10 nm to 40 nm diameter were prepared by flame spray pyrolysis. These particles were subsequently used with stitching material and method of the disclosure to form a porous particulate film and as described below.

PARTICLE FILM FORMATION—GLASS SUBSTRATE Silane 1 of Example 1 was reacted with a suspension of tungsten oxide particles in N-methylpyrolidinone (NMP). Thus, for example, a suspension of tungsten oxide particles (6 g) in NMP (about 10 mL) was sonicated for 20 min. Trimethoxysilylpropyltrichlorosilane, 1, (14.7 microL) in NMP (1 mL) was then added and the mixture shaken vigorously for 2 min. An aliquot of the suspension was then placed on a fluorinated tin oxide (FTO) coated glass substrate and spread into a thin (about 75 micrometers) film. This film was then heated from below on a hotplate set to about 100° C. for 1 hour, after which time the temperature was reduced to room temperature. The film formed and bound to the substrate. The bound film may be further functionalized if desired with, for example, an electrochromic dye to enhance color change.

ELECTROCHROMIC DEVICE FABRICATION A tungsten oxide particle film on the FTO coated glass substrate prepared above was sealed to a counter-electrode assembly consisting of fluorine doped tin oxide (FTO) on soda lime glass. A gap of about 20 to 100 micrometers was left between the two electrodes into which an electrolyte containing about 1M lithium triflate in acetonitrile was added. The gap was then sealed with epoxy.

ELECTROCHROMIC DEVICE EVALUATION The tungsten oxide particle film cell constructed above was connected to a variable voltage DC electrical supply. A potential of about 1.5 V was applied across the device. A color change from the base color, faint blue-grey tint, to an intense dark blue-grey, was observed after about 1 minute. Further darkening occurred during several additional minutes. The pronounced change was stable upon removal of the applied potential. Upon reversal of the potential bias the dark color dissipated and returned to the original faint blue-grey tint color of the device. This process was repeated several times and there was no discernible difference in the reproducibility of the response or performance between cycles (photo records not shown). Although not limited by theory the performance is believed to be so slow due to the presence of alternate pathways for the electrons across the device, i.e., other than through the tungsten oxide. Alternative device designs may overcome this performance issue.

The disclosure has been described with reference to various specific embodiments and techniques. However, it should be understood that many variations and modifications are possible while remaining within the spirit and scope of the disclosure.

What is claimed is:

1. A composition comprising the reaction product of:
a compound of formula (I)

where
$R^1$ is a divalent spacer group selected from saturated or unsaturated —$(C_1-C_{20})$ alkylene-, $(C_1-C_4)$alkyl substituted saturated or unsaturated —$(C_1-C_{20})$ alkylene-, —Ar—, $(C_1-C_4)$alkyl substituted —Ar—, —$(CH_2)_k$—Ar—$(CH_2)_k$—, $(C_1-C_4)$alkyl substituted —$(CH_2)_k$—Ar—$(CH_2)_k$—, —Ar—Ar—, $(C_1-C_4)$alkyl substituted —Ar—Ar—, —$(CH_2)_k$—Ar—Ar—$(CH_2)_k$—, $(C_1-C_4)$alkyl substituted —$(CH_2)_k$—Ar—Ar—$(CH_2)_k$—, —$(CH_2)_k$—Ar—$(CH_2)_k$—Ar—$(CH_2)_k$—, $(C_1-C_4)$alkyl substituted —$(CH_2)_k$—Ar—$(CH_2)_k$—Ar—$(CH_2)_k$—, —Ar—O—Ar—, $(C_1-C_4)$alkyl substituted —Ar—O—Ar—, —$(CH_2)_k$—Ar—O—Ar—$(CH_2)_k$—, $(C_1-C_4)$ alkyl substituted —$(CH_2)_k$—Ar—O—Ar—$(CH_2)_k$—, Het, $(C_1-C_4)$alkyl substituted —Het—, —$(CH_2)_k$—Het—, $(C_1-C_4)$alkyl substituted —$(CH_2)_k$—Het—, —$(CH_2)_k$—Het—$(CH_2)_k$—, $(C_1-C_4)$alkyl substituted —$(CH_2)_k$—Het—$(CH_2)_k$—, —Ar—$(CH_2)_k$—, $(C_1-C_4)$ alkyl substituted —Ar'—$(CH_2)_k$—, Ar'—CH=, $(C_1-C_4)$alkyl substituted Ar'—CH=, an amine of the formula —$NR^3$—, or a diamine of the formula —$NR^3$—$R^1$—$NR^3$— where each $R^3$ is independently H, or saturated or unsaturated —$(C_1-C_4)$ alkyl;
Ar is aryl,
Het is heteroaryl,
k is 1 to 20,
$R^2$ is a monovalent group each independently a branched or unbranched, saturated or unsaturated —$(C_1-C_6)$alkyl, —Ar or $(C_1-C_4)$alkyl substituted —Ar; and
X is halo; and
a metal oxide particle.

2. The composition of claim 1 wherein the compound of formula (I) is $(CH_3O)_3Si$—$CH_2$—$CH_2$—$CH_2$—$SiCl_3$ or $(CH_3O)_3Si$—$C_6H_5$—$SiCl_3$, and the metal oxide particle comprises at least one of silica, titania, alumina, tin, tungsten, iron, or mixtures thereof.

3. The composition of claim 1 further comprising a substrate that reacts with and supports the reaction product, the substrate comprising at least one of a glass, a polymer, a ceramic, a ceramer, a composite, or combinations thereof.

4. A composition comprising the reaction product of:
a compound of formula (I)

where
$R^1$ is a divalent spacer group selected from saturated or unsaturated —$(C_1-C_{20})$ alkylene-, $(C_1-C_4)$alkyl substituted saturated or unsaturated —$(C_1-C_{20})$ alkylene-, —Ar—, $(C_1-C_4)$alkyl substituted —Ar—, —$(CH_2)_k$—Ar—$(CH_2)_k$—, $(C_1-C_4)$alkyl substituted —$(CH_2)_k$—Ar—$(CH_2)_k$—, —Ar—Ar—, $(C_1-C_4)$alkyl substituted —Ar—Ar—, —$(CH_2)_k$—Ar—Ar—$(CH_2)_k$—, $(C_1-C_4)$ alkyl substituted —$(CH_2)_k$—Ar—Ar—$(CH_2)_k$—, —$(CH_2)_k$—Ar—$(CH_2)_k$—Ar—$(CH_2)_k$—, $(C_1-C_4)$alkyl substituted —$(CH_2)_k$—Ar—$(CH_2)_k$—Ar—$(CH_2)_k$—, —Ar—O—Ar—$(C_1-C_4)$alkyl substituted —Ar—O—Ar—, —$(CH_2)_k$—Ar—O—Ar—$(CH_2)_k$—, $(C_1-C_4)$ alkyl substituted —$(CH_2)_k$—Ar—O—Ar—$(CH_2)_k$—, Het, $(C_1-C_4)$alkyl substituted —Het—, —$(CH_2)_k$—Het—, $(C_1-C_4)$alkyl substituted —$(CH_2)_k$—Het —, —$(CH_2)_k$—Het—$(CH_2)_k$—, $(C_1-C_4)$alkyl substituted —$(CH_2)_k$—Het—$(CH_2)_k$—, —Ar—$(CH_2)_k$—, $(C_1-C_4)$ alkyl substituted —Ar—$(CH_2)_k$—, Ar'—CH=, $(C_1-C_4)$ alkyl substituted Ar'—CH=, an amine of the formula —$NR^3$—, or a diamine of the formula —$NR^3$—$R^1$—$NR^3$— where each $R^3$ is independently H, or saturated or unsaturated —$(C_1-C_4)$ alkyl;

Ar is aryl,

Het is heteroaryl, k is 1 to 20, $R^2$ is a monovalent group each independently a branched or unbranched, saturated or unsaturated —$(C_1-C_6)$alkyl, —Ar or $(C_1-C_4)$alkyl substituted —Ar; and X is halo; and a metal oxide particle, wherein the reaction product comprises a network of metal oxide particles joined together by a bis-silane spacer of the formula =Si—$R^1$—Si=.

5. The composition of claim 3, further comprising a dye.

6. A composition comprising the reaction product of:

a compound of formula (I)

$$(R^2O)_3Si—R^1—SiX_3 \qquad (I)$$

where $R^1$ is a divalent spacer group selected from saturated or unsaturated —$(C_1-C_{20})$ alkylene-, $(C_1-C_4)$alkyl substituted saturated or unsaturated —$(C_1-C_{20})$ alkylene-, —Ar—, $(C_1-C_4)$alkyl substituted —Ar—, —$(CH_2)_k$—Ar—$(CH_2)_k$—, $(C_1-C_4)$alkyl substituted —$(CH_2)_k$—Ar—$(CH_2)_k$—, —Ar—Ar—, $(C_1-C_4)$alkyl substituted —Ar—Ar—, —$(CH_2)_k$—Ar—Ar—$(CH_2)_k$—, $(C_1-C_4)$alkyl substituted —$(CH_2)_k$—Ar—Ar—$(CH_2)_k$—, —$(CH_2)_k$—Ar—$(CH_2)_k$—Ar—$(CH_2)_k$—, $(C_1-C_4)$alkyl substituted —$(CH_2)_k$—Ar—$(CH_2)_k$—Ar—$(CH_2)_k$—, —Ar—O—Ar—$(C_1-C_4)$alkyl substituted —Ar—O—Ar—, —$(CH_2)_k$—Ar—O—Ar—$(CH_2)_k$—, $(C_1-C_4)$alkyl substituted —$(CH_2)_k$—Ar—O—Ar—$(CH_2)_k$—, Het, $(C_1-C_4)$alkyl substituted —Het—, —$(CH_2)_k$—Het—, $(C_1-C_4)$alkyl substituted —$(CH_2)_k$—Het—, —$(CH_2)_k$—Het—$(C_1-C_4)$alkyl substituted —$(CH_2)_k$—Het—$(CH_2)_k$—, —Ar—$(CH_2)_k$—, $(C_1-C_4)$alkyl substituted —Ar—$(CH_2)_k$—, Ar'—CH=, $(C_1-C_4)$alkyl substituted Ar'—CH=, an amine of the formula —$NR^3$—, or a diamine of the formula —$NR^3$—$R^1$—$NR^3$— where each $R^3$ is independently H, or saturated or unsaturated —$(C_1-C_4)$ alkyl;

Ar is aryl,

Het is heteroaryl, k is 1 to 20, $R^2$ is a monovalent group each independently a branched or unbranched, saturated or unsaturated —$(C_1-C_6)$alkyl, —Ar or $(C_1-C_4)$alkyl substituted —Ar; and X is halo; and a metal oxide particle, wherein the reaction product comprises a first formed product comprised of the metal oxide particles having =Si—$R^1$—Si(OR)$_3$ groups attached to the particles, and a subsequent second reaction product comprised of an interconnected network of the metal oxide particles joined by a bis-silane spacer of the formula =Si—$R^1$—Si=.

7. The composition of claim 4 wherein the compound of formula (I) is $(CH_3O)_3Si$—$CH_2$—$CH_2$—$CH_2$—$SiCl_3$ or $(CH_3O)_3Si$—$C_6H_5$—$SiCl_3$, and the metal oxide particle comprises at least one of silica, titania, alumina, tin, tungsten, iron, or mixtures thereof.

8. The composition of claim 4 further comprising a substrate that reacts with and supports the reaction product, the substrate comprising at least one of a glass, a polymer, a ceramic, a ceramer, a composite, or combinations thereof.

9. The composition of claim 4, further comprising a dye.

10. The composition of claim 6 wherein the compound of formula (I) is $(CH_3O)_3Si$—$CH_2$—$CH_2$—$CH_2$—$SiCl_3$ or $(CH_3O)_3Si$—$C_6H_5$—$SiCl_3$, and the metal oxide particle comprises at least one of silica, titania, alumina, tin, tungsten, iron, or mixtures thereof.

11. The composition of claim 6 further comprising a substrate that reacts with and supports the reaction product, the substrate comprising at least one of a glass, a polymer, a ceramic, a ceramer, a composite, or combinations thereof.

12. The composition of claim 6, further comprising a dye.

\* \* \* \* \*